United States Patent [19]

Burstein et al.

[11] Patent Number: 5,015,248
[45] Date of Patent: May 14, 1991

[54] BONE FRACTURE FIXATION DEVICE

[75] Inventors: Albert H. Burstein, Stamford, Conn.; Jeffrey S. Bennett, Fort Lee, N.J.

[73] Assignee: New York Society for the Relief of the Ruptured & Crippled, Maintaining the Hospital for Special Surgery, New York, N.Y.

[21] Appl. No.: 536,172

[22] Filed: Jun. 11, 1990

[51] Int. Cl.$^5$ .............................................. A61F 5/00
[52] U.S. Cl. ......................................... 606/74; 606/69; 606/72
[58] Field of Search ...................... 128/69; 606/69, 72, 606/70, 71, 74

[56] References Cited

U.S. PATENT DOCUMENTS

| | | | |
|---|---|---|---|
| 1,950,799 | 3/1934 | Jones | 606/74 |
| 3,824,995 | 7/1974 | Getscher et al. | 606/69 |
| 4,146,022 | 3/1979 | Johnson et al. | 606/74 |
| 4,263,904 | 4/1981 | Judet | 606/69 X |
| 4,364,382 | 12/1982 | Mennen | 606/69 |
| 4,524,765 | 6/1985 | de Zbikowski | 606/69 |
| 4,565,193 | 1/1986 | Streli | 606/69 |
| 4,573,458 | 3/1986 | Lower | 606/69 |
| 4,651,724 | 3/1987 | Berentey et al. | 606/69 |
| 4,705,031 | 11/1987 | Wolter | 606/69 |
| 4,955,886 | 9/1990 | Pawlok | 606/69 |

FOREIGN PATENT DOCUMENTS

| | | | |
|---|---|---|---|
| 0014823 | 9/1980 | European Pat. Off. | 606/69 |
| 2435243 | 5/1980 | France | 606/69 |
| 0199330 | 7/1967 | U.S.S.R. | 606/74 |
| 0632351 | 11/1978 | U.S.S.R. | 606/74 |
| 1037911 | 8/1983 | U.S.S.R. | 606/69 |

OTHER PUBLICATIONS

Sluss, *Emergency Surgery*, p. 581, Blakiston's, Son & Co., Phila., 1931.

Primary Examiner—Richard J. Apley
Assistant Examiner—Linda C. M. Dvorak
Attorney, Agent, or Firm—Brumbaugh, Graves, Donohue & Raymond

[57] ABSTRACT

A bone fracture fixation device for stabilizing a fracture of a portion of a long bone overlying or closely adjacent to a prosthetic joint component comprises a fixation plate that is held adjacent to the bone by clamps joined to it by screws. The fixation plate and clamps have spikes that penetrate partly into the bone to fix the bone to the device and stabilize the fracture but that also remain partly outside the bone and serve as spacers to hold the plate and clamps spaced apart from the bone, thereby leaving the periosteum undisturbed and preserving good blood distribution to the bone at the fracture site and hence good conditions for healing of the fracture.

7 Claims, 4 Drawing Sheets

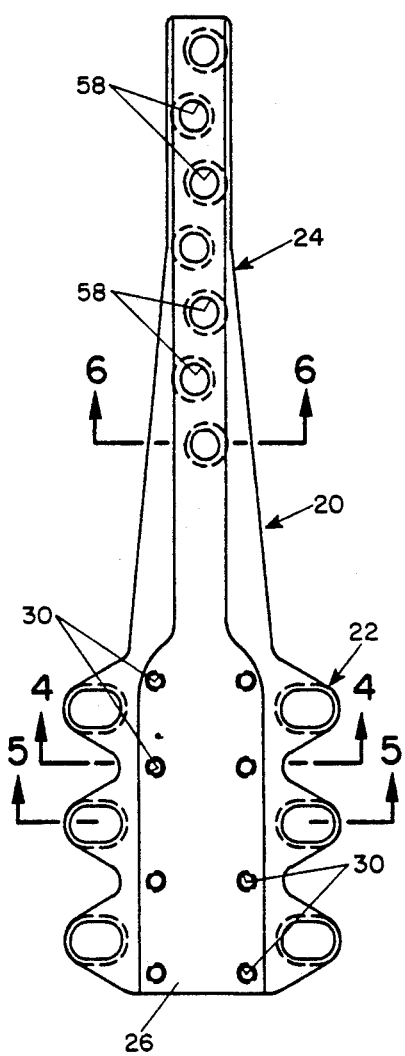
FIG. 1
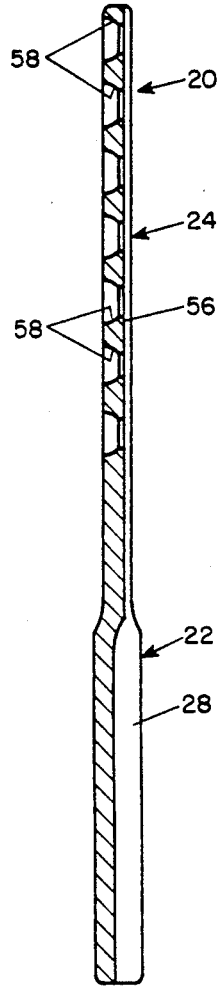
FIG. 3
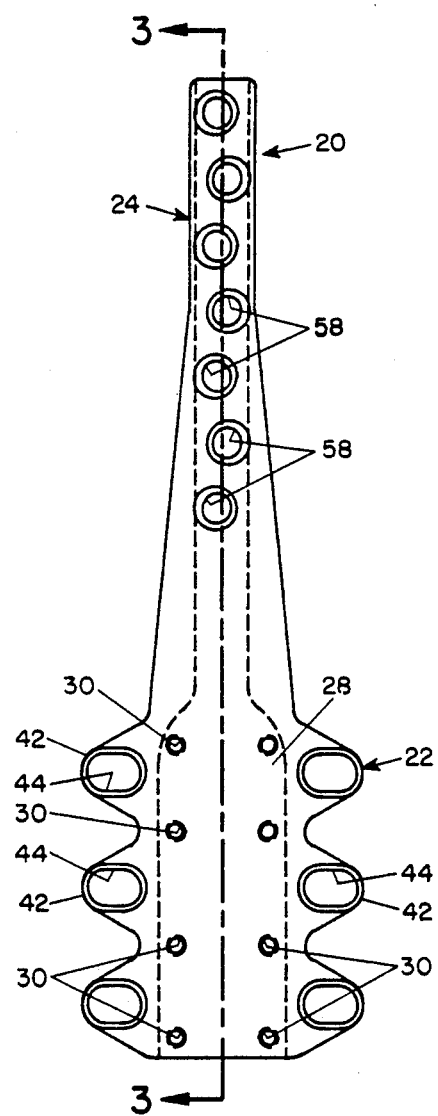
FIG. 2
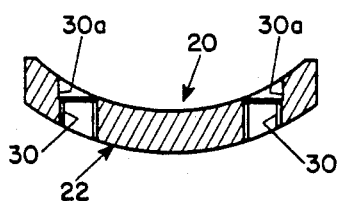
FIG. 4
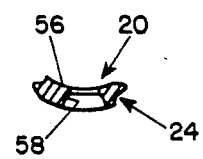
FIG. 6
FIG. 5

BONE FRACTURE FIXATION DEVICE

BACKGROUND OF THE INVENTION

Over about the past 20 years or so, it has become increasingly common to treat diseased and injured bone joints by implanting prosthetic joints. The prostheses for joints involving the long bones, such as the femur, tibia, humerus, radius and ulna often have stem portions that extend some distance into the medullary canals of the bone shafts. Not infrequently, a person with a joint prosthesis sustains a fracture in a portion of the bone that wholly or partly overlies the prosthetic component or is closely adjacent to it.

The conventional treatment of such fractures involves immobilization of the joint while the fracture heals. If the fracture overlies the prosthesis, the prosthesis will usually be replaced. The replacement of the prosthesis and the immobilization of the joint are both detrimental to the patient, in that a revision prosthesis is often not as successful as the original one, and immobilization of the joint slows the healing process and can cause permanently reduced function and even loss of function. At the very least immobilization of the joint greatly increases the time and effort required for rehabilitation.

SUMMARY OF THE INVENTION

An object of the invention is to provide a way of treating a fracture of a portion of a long bone proximate to a joint prosthesis that avoids replacement of the prosthesis. A further object is to provide a device that stabilizes the fracture so that it can heal and that does not require immobilization of the joint, thereby enhancing the healing process by preserving good blood flow to the fracture site, minimizing the possibility of reduction or loss of function by allowing the patient to exercise the joint while the fracture is healing, and considerably easing and speeding up the patient's rehabilitation after the fracture heals.

The foregoing objects are attained, according to the present invention, by a fracture fixation device comprising the following components: an elongated fixation plate having a clamp portion adapted to be disposed adjacent a lengthwise segment of the bone overlying the implant proximate to the fracture and having a multiplicity of spikes projecting from the clamp portion and adapted to penetrate partway into the bone and hold the fixation plate stationary relative to and spaced apart from the bone and at least two screw holes in each side marginal portion, each of the screw holes in one side being arranged transversely substantially opposite a screw hole in the other side with respect to the longitudinal axis of the fixation plate to thereby form opposite hole pairs; at least two clamps, each being generally C-shaped and being adapted to embrace partly the bone in a position on the opposite side thereof from the clamp portion of the fixation plate, and each having at least two spikes adapted to penetrate partway into the bone and hold the clamp stationary relative to and spaced apart from the bone and a hole in each end located to be in alignment with each hole of a hole pair in the fixation plate; and threaded fasteners passing through the holes in the fixation plate and into the holes in the clamps and joining the clamps to the fixation plate.

In a preferred embodiment the fixation plate is symmetrical about a longitudinal axis, and the spikes on the fixation plate are arranged in pairs symmetrically on opposite sides of the longitudinal axis of the plate and have their axes oriented parallel to each other.

In one form of the fixation plate there is a plate portion having a multiplicity of holes spaced apart lengthwise from the screw holes and adapted to receive cortical bone screws, the holes preferably being arranged in staggered relation on opposite sides of a longitudinal axis of the fixation plate and those on one side being oblique to those on the other side at a small included angle. The plate portion is fastened by the cortical bone screws to the bone.

In another form the fixation plate has a first set of at least two pairs of screw holes adjacent one end and a second set of at least two pairs of screw holes adjacent the other end, the two sets of screw holes being longitudinally spaced-apart to define a bridge portion of the plate adapted to overlie a bone fracture. There are no spikes in the bridge portion.

In still another form which is used for fractures of the proximal femur, the fixation plate has a generally J-shaped hook portion at one end, the tip of the hook portion being bifurcated to form two prongs projecting inferiorly, each of which has a sharp tooth end adapted to penetrate into the superior aspect of the greater trochanter.

The invention stabilizes the fracture mainly by bridging it with the fixation plate, which is clamped or screwed to a portion or portions of the bone on one or both sides of the fracture longitudinally of the bone, and to which the bone is fixed by spikes. With oblique or spiral bone fractures, the clamp portions of the fixation plate may partly overlie the fracture. The portions of the fixation plate that overlie the fracture are spaced apart from the bone, inasmuch as the spikes penetrate only a small distance, 1.0 to 1.5 mm, into the bone, leaving some of each spike exposed outside the bone surface to serve as a spacer. The spacing of the fixation plate and clamps from the bone leaves the periosteum undisturbed and preserves good blood distribution to the part of the bone around the fracture site and hence good conditions for healing of the fracture.

DESCRIPTION OF THE DRAWINGS

FIG. 1 is a plan view of the internal aspect (the aspect that faces toward the bone) of a clamp/plate;

FIG. 2 is a view of the external aspect of the clamp/plate;

FIG. 3 is a longitudinal cross-sectional view of the clamp/plate;

FIGS. 4 to 6 are cross-sectional views of the clamp/plate taken along the correspondingly numbered lines of FIG. 1, FIG. 4 being on an enlarged scale;

DESCRIPTION OF THE EMBODIMENTS

The fixation device takes on different forms, depending upon the location of the fracture being treated, but common to all forms is an elongated fixation plate that is received on one side of the bone and has a clamp portion, two or more clamps that are received on the other side of the bone, and screws joining the clamp portion of the fixation plate to the clamps and drawing them toward each other with the bone between them. Spikes on the clamp portion of the fixation plate and on each clamp penetrate a small distance into the bone and stabilize the bone relative to the fixation device.

Figure 18:
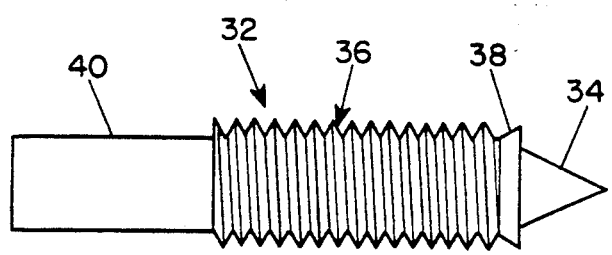
FIG. 18 is an elevational view of a spike in its manufactured form.

The clamp/plate 20 shown in FIGS. 1 to 6 is one form of fixation plate and consists of a clamp portion 22 and a plate portion 24. It is designed for use in stabilizing a bone fracture proximate to the tip end of the stem portion of a joint prosthesis component. The clamp portion 22 has a transversely curved center portion 26, the concave surface 28 of which faces inwardly toward the bone and approximately matches the circumferential curvature of the portion of the bone shaft lying outwardly of the stem of the prosthesis. Near each lateral margin of the center portion 26 of the clamp portion 22 are several spaced-apart threaded holes 30, each of which receives a spike 32 (see FIG. 18). As will become apparent below, all embodiments of the present invention shown in the drawings have spikes that are manufactured separately from the fixation plates and are installed in threaded holes, but the spikes can be joined to the plates and clamps in other ways and can also be integral with the plates and clamps.

As manufactured (see FIG. 18), each spike 32 has a conical point 34 having a cone angle in the range of 30° to 60°, preferably 40°, an externally threaded shank 36 formed with a tapered shoulder 38 at the juncture with the tip and a neck 40 projecting from the end of the shank. The spikes 32 are threaded into the holes 30, tightened with a suitable tool applied to the neck 40, and are then cut off, ground and polished so that their external ends are flush with the external surface of the clamp portion 22 (see FIG. 19). The holes 30 have a tapered shoulder 30a against which the shoulders 38 of the spikes bear. The axes of the holes 30 are perpendicular to a plane tangent to the curved center portion 26 at the longitudinal center axis. Accordingly, when the clamp/plate is drawn toward the femur, the tips of at least some of the spikes 32 penetrate by movement along their axes a small distance into the bone, say, about 1.0 to 1.5 mm, and hold the clamp/plate stationary relative to the bone.

Figure 19:
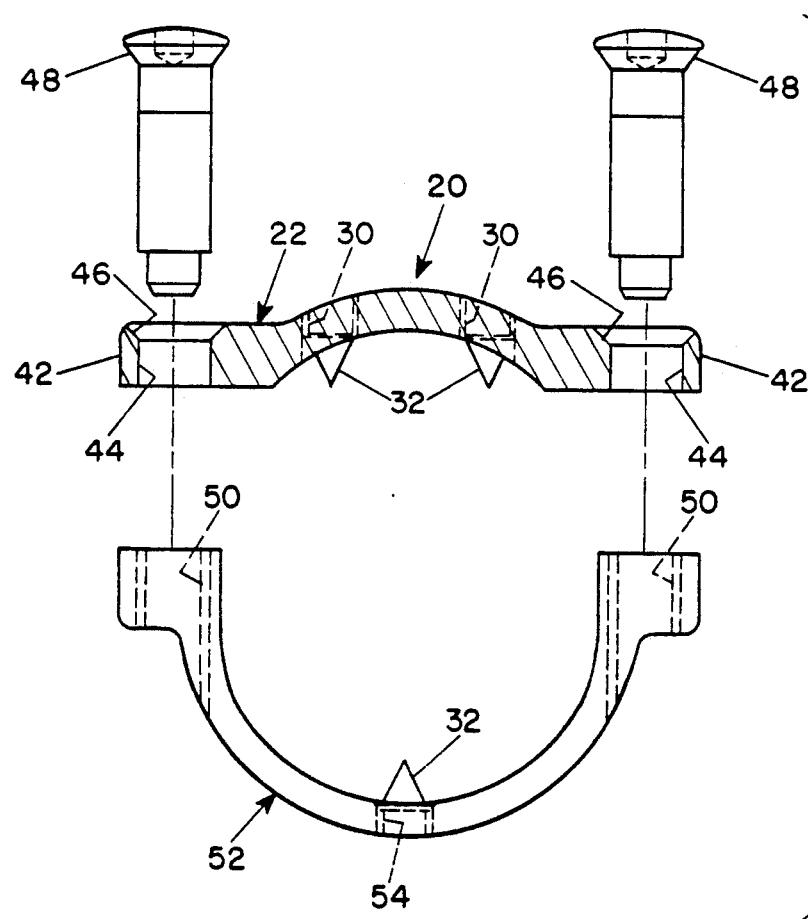
FIG. 19 is an exploded view illustrating how the device is assembled.

Extending laterally out from either side of the clamp portion 22 of the clamp/plate 20 are lugs 42, each of which has a laterally elongated, countersunk hole 44 that presents an outwardly facing shoulder 46 (see FIGS. 5 and 19). The lugs are arranged opposite each other in pairs, and the pairs of holes are axially spaced apart. Each hole 44 receives the head end of an oval-head allen-type machine screw 48 (see FIG. 19).

Figures 7, 8, 9, 10:
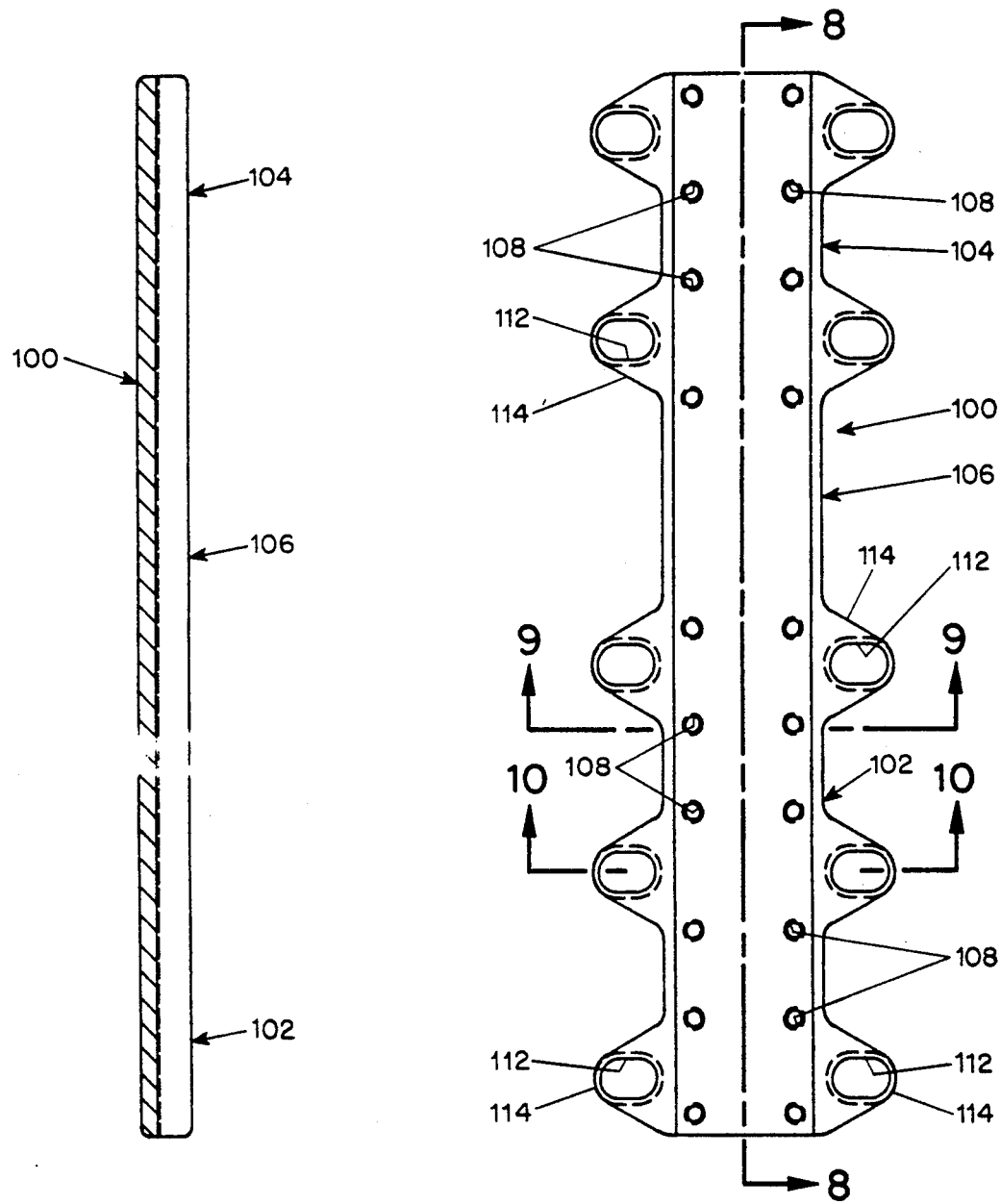
FIG. 7 is a plan view of the internal aspect of a clamp/clamp.
FIG. 8 is a longitudinal cross-sectional view taken along the lines 8—8 of FIG. 7 of the clamp/clamp.
FIGS. 9 and 10 are transverse cross-sectional views of the clamp/clamp (FIG. 9 being on an enlarged scale) taken along the correspondingly numbered lines of FIG. 7.
Figure 11:
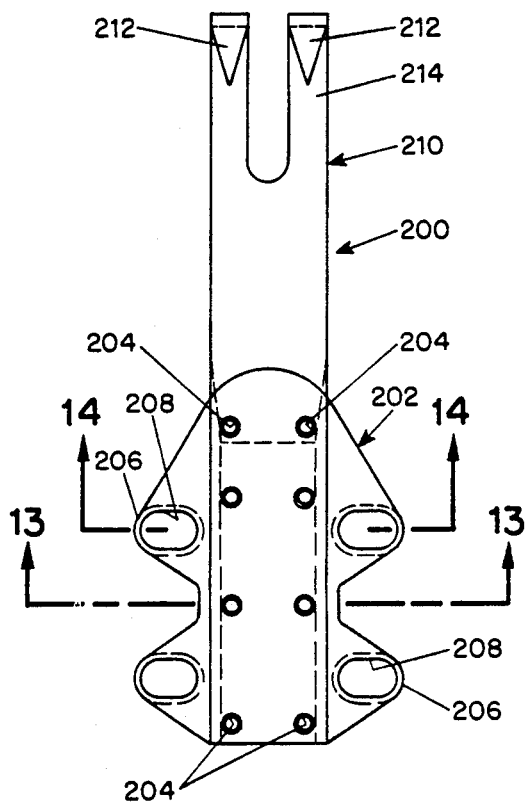
FIG. 11 is a plan view of the internal aspect of a clamp/hook.
Figure 12:
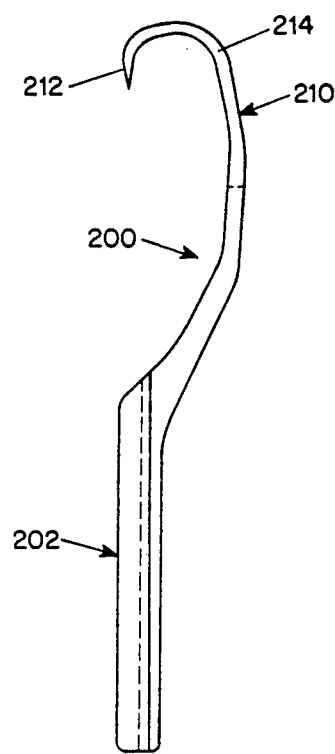
FIG. 12 is a side elevational view of the clamp/hook.
Figure 13:
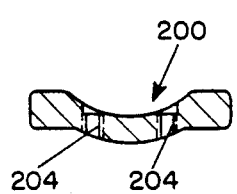
FIGS. 13 and 14 are transverse cross-sectional views of the clamp/hook taken along the correspondingly numbered lines of FIG. 11, FIG. 13 being on an enlarged scale.
Figure 15:
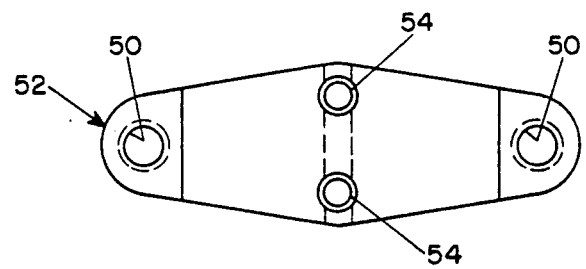
FIG. 15 is a plan view of the internal aspect of a clamp.
Figure 14:
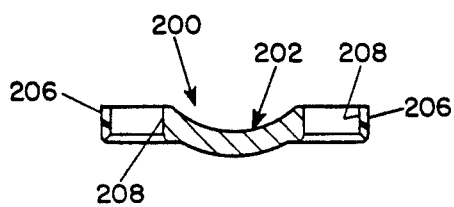
Figure 16:
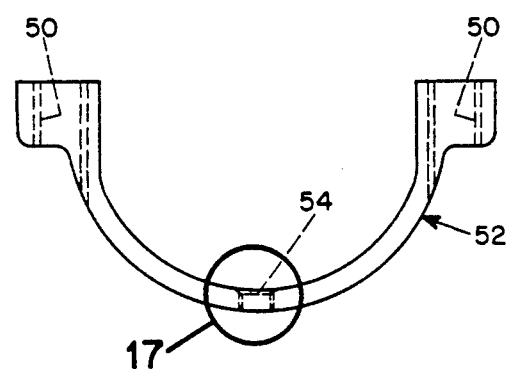
FIG. 16 is a side elevational view of the clamp.
Figure 17:
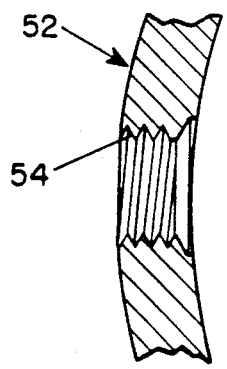
FIG. 17 is an enlarged detail cross-sectional view of the part of the clamp circled in FIG. 16.

The threaded ends of the screws 48 are received in threaded holes 50 in clamps 52 (see FIGS. 15 and 16), one such clamp 52 being provided for each pair of holes 42 in the clamp portion 22 of the clamp/plate 20. The clamps 52 are generally U-shaped and have threaded holes 54 (see FIG. 17) that receive spikes 32 (see FIGS. 18 and 19). The spikes of the clamps 52 penetrate axially a small distance into the bone and, in conjunction with the spikes of the clamp/plate 20, stabilize the bone against displacement relative to the clamp/plate. The clamps are made in a range of sizes in order to conform to the size and taper of the patient's bone, but the elongated holes 44 allow several sizes of clamps to be used with the clamp/plate 20.

The plate portion 24 of the clamp/plate 20 is transversely curved so as to present a concave internal surface 56 to the bone shaft. Countersunk, staggered holes 58 oriented obliquely to each other at a small angle, 10° being suitable, receive standard cortical bone screws (not shown). The screws fasten the plate portion 24 of the clamp/plate to the bone shaft. The screw holes 58 are spaced apart from the clamp portion 22 of the clamp/plate to ensure that the cortical bone screws are received in sound bone remote from the fracture site, which will often be just distal or proximal to the tip of the stem of a joint prosthesis component. The clamp portion 22 of the clamp/plate 20 and the clamps 52 will be positioned around the portion of the bone shaft that receives the prosthesis stem. The clamp/plate 20 bridges the fracture, and because both the plate portion and the clamp portion are fixed to the bone shaft on opposite sides of the fracture, the fracture is stabilized. As the fracture heals, the patient can exercise the joint add thereby maintain good blood circulation and retain joint mobility. The fixation device can remain in the patient's bone permanently. In time, the bone around the spikes will remodel.

The clamp/clamp form of fixation plate 100 shown in FIGS. 7 to 10 is designed for use in stabilizing a fracture around the stem of a component of a joint prosthesis implanted in a long bone. It has two clamp portions 102 and 104 separated by a bridge portion 106, which is, when possible, positioned to overlie the fracture site. The clamp/clamp can be inverted end to end to best suit the geometry and location of the fracture. Threaded holes 108 in the transversely curved body portion 110 receive the spikes 32. Elongated holes 112 in outwardly extending tabs 114 receive the screws 48 by which the clamps 52 are fastened to the clamp/clamp 100.

The clamp/hook form of fixation plate 200 (FIGS. 11 to 14) is designed for stabilizing a fracture or non-union of the greater trochanter of the proximal femur. It has a clamp portion 202 having holes 204 for the spikes 32 and two pairs of lugs 206, each with a transversely elongated hole 208 for a screw 48. The clamp portion 202 and two clamps 52 are fitted to the proximal femur around the stem of the femoral hip joint prosthesis. A J-shaped hook portion 210 extends up from the clamp portion. Downwardly extending, sharp teeth 212 on the bifurcated upper end portion 214 of the hook portion 210 are set a small distance into the superior aspect of the greater trochanter prior to tightening the clamps.

The drawings show the fixation plates as longitudinally straight, which is the way they are, preferably and conveniently, manufactured. After manufacture they may be bent so as to conform approximately with the lengthwise curvature of the aspect of the portion of the bone to which they will be adjacent.

As alluded to above, it is not necessary for all of the spikes of the fixation plates and clamps of the fixation device to penetrate or even touch the bone. Generally, however both spikes of each clamp will penetrate the bone, because the screws can pivot a few degrees circumferentially and axially in the holes in the clamp portions of the plates and thereby permit the spikes of the clamps to be set into the bone by moving the clamps to cock them relative to the fixation plate. All components of the device may be made of Ti-6A1-4V or some other suitable implantable alloy. All forms of the fixation plate may be symmetrical about a longitudinal axis, so they can be used in both right and left bones, but they may be asymmetrical, if desired.

Most surgeons will choose to place the fixation plate adjacent the lateral aspect of the bone, simply because the surgical procedure will be a little easier. The clamps and plates are placed adjacent the bone, the screws are installed and slightly tightened, special C-clamps are applied to the plates and clamps and worked to set the spikes into the bone, and the screws are then tightened to hold the fixation device clamped to the bone.

I claim:

1. A bone fracture fixation device for use in stabilizing a fracture in a portion of a long bone that overlies or is proximate to a prosthetic joint component comprising an elongated fixation plate having a clamp portion including a center region and two side margins, the center region being adapted to be disposed adjacent a lengthwise segment of the bone overlying the implant proximate to the fracture, a multiplicity of spikes projecting from the clamp portion and adapted to penetrate partway into the bone and hold the fixation plate stationary relative to and spaced apart from the bone, at least two screw holes in each side margin of the clamp portion, each of the screw holes in one side margin being arranged transversely substantially opposite a screw hole in the other side margin with respect to the longitudinal axis of the fixation plate to thereby form opposite hole pairs, at least two clamps, each being generally C-shaped and being adapted to embrace partly the bone in a position on the opposite side thereof from the clamp portion of the fixation plate, at least two spikes projecting from each clamp and being adapted to penetrate partway into the bone and hold the clamp stationary relative to and spaced apart from the bone, a threaded hole in each end of each clamp located so as to be in alignment with a hole pair in the fixation plate, and threaded fasteners passing through the screw holes in the fixation plate and into the threaded holes in the clamps and joining the clamps to the fixation plate.

2. A bone fracture fixation device according to claim 1 wherein the fixation plate is symmetrical about a longitudinal axis.

3. A bone fracture fixation device according to claim 1 wherein the spikes on the fixation plate are arranged in pairs symmetrically on opposite sides of a longitudinal center axis of the plate and have their axes oriented parallel to each other.

4. A bone fracture fixation device according to claim 1 wherein the fixation plate further includes a plate portion having a multiplicity of holes spaced apart lengthwise from the screw holes and adapted to receive cortical bone screws.

5. A bone fracture fixation device according to claim 4 wherein the holes are arranged in staggered relation on opposite sides of a longitudinal axis of the plate portion and those on one side are oblique to those on the other side at a small included angle.

6. A bone fracture fixation device according to claim 1 wherein the fixation plate has a first clamp portion adjacent one end and a clamp portion adjacent the other end, the clamp portions being longitudinally spaced-apart to define a bridge portion of the fixation plate between them that is adapted to overlie a bone fracture, and wherein there are no spikes in the bridge portion.

7. A bone fracture fixation device according to claim 1 wherein the fixation plate has a generally J-shaped hook portion at one end, the tip of the hook portion being bifurcated to form two prongs projecting inferiorly, each of which has a sharp tooth end adapted to penetrate into the superior aspect of the greater trochanter.

* * * * *